United States Patent [19]

Bierman

[11] Patent Number: 5,800,402

[45] Date of Patent: Sep. 1, 1998

[54] CATHETER ANCHORING SYSTEM AND METHOD OF USE

[75] Inventor: Steven F. Bierman, Del Mar, Calif.

[73] Assignee: Venetec International, Inc., Mission Viejo, Calif.

[21] Appl. No.: 644,208

[22] Filed: May 10, 1996

Related U.S. Application Data

[63] Continuation-in-part of Ser. No. 223,948, Apr. 6, 1994, Pat. No. 5,578,013, which is a continuation-in-part of Ser. No. 121,942, Sep. 15, 1993, Pat. No. 5,456,671, which is a continuation-in-part of Ser. No. 34,340, Mar. 19, 1993, Pat. No. 5,354,282.

[51] Int. Cl.$^6$ .................................................. A61M 5/32
[52] U.S. Cl. .................... 604/180; 604/174; 128/DIG. 26
[58] Field of Search ............................. 604/174, 179, 604/180, 178; 128/DIG. 26

[56] References Cited

U.S. PATENT DOCUMENTS

| | | |
|---|---|---|
| D. 256,162 | 7/1980 | Haerr et al. . |
| D. 273,993 | 5/1984 | Schulte et al. . |
| D. 302,304 | 7/1989 | Kulle et al. . |
| D. 310,721 | 9/1990 | Beisang, III . |
| D. 323,390 | 1/1992 | Paine et al. . |
| D. 347,060 | 5/1994 | Bierman . |
| 2,525,398 | 10/1950 | Collins . |
| 2,533,961 | 12/1950 | Rousseau et al. . |
| 2,707,953 | 5/1955 | Ryan . |
| 3,064,648 | 11/1962 | Bujan . |
| 3,167,072 | 1/1965 | Stone et al. . |
| 3,245,567 | 4/1966 | Knight . |
| 3,394,954 | 7/1968 | Sarns . |
| 3,529,597 | 9/1970 | Fuzak . |
| 3,677,250 | 7/1972 | Thomas . |
| 3,686,896 | 8/1972 | Rutter . |
| 3,766,915 | 10/1973 | Rychlik . |
| 3,856,020 | 12/1974 | Kovac . |
| 3,900,026 | 8/1975 | Wagner . |
| 3,906,946 | 9/1975 | Nordstrom . |
| 3,920,001 | 11/1975 | Edwards . |
| 3,942,228 | 3/1976 | Buckman et al. . |
| 3,973,565 | 8/1976 | Steer . |
| 4,020,835 | 5/1977 | Nordstrom et al. . |
| 4,059,105 | 11/1977 | Cutruzzula et al. . |

(List continued on next page.)

FOREIGN PATENT DOCUMENTS

| | | |
|---|---|---|
| 247590A2 | 2/1987 | European Pat. Off. . |
| 263789A1 | 4/1988 | European Pat. Off. . |
| 356683A | 3/1990 | European Pat. Off. . |
| 367549A3 | 5/1990 | European Pat. Off. . |
| 2063679 | 6/1981 | United Kingdom . |
| 2086466 | 5/1982 | United Kingdom . |
| 9005559 | 5/1990 | WIPO . |
| 9116939 | 11/1991 | WIPO . |
| 9203070 | 4/1992 | WIPO . |
| 9203923 | 5/1992 | WIPO . |

*Primary Examiner*—Sam Rimell
*Assistant Examiner*—Luke Yeh
*Attorney, Agent, or Firm*—Knobbe, Martens, Olson & Bear, LLP

[57] ABSTRACT

A catheter anchoring device is provided for securely anchoring a catheter to a patient's skin. The catheter anchoring device is particularly well suited to secure an epidural catheter proximate to an insertion site. The catheter anchoring device includes a plurality of channels which receive a section of the catheter body such that a portion of the received section of the catheter body lies generally transverse to an axis defined by the indwelling portion of the catheter. An additional anchoring device also can be used to anchor a catheter/fluid supply tube interconnection to the skin of a patient. In connection with epidural catheterization, one anchoring device can be attached to the anterior of the patient's torso, and the other anchoring device can be positioned on the posterior of the patient's torso and proximate to the point of insertion. This arrangement improves the comfort of the patient and makes the interconnection between the catheter and the fluid tube more readily accessible.

46 Claims, 10 Drawing Sheets

U.S. PATENT DOCUMENTS

| | | |
|---|---|---|
| 4,082,094 | 4/1978 | Dailey . |
| 4,114,618 | 9/1978 | Vargas . |
| 4,123,091 | 10/1978 | Cosentino et al. . |
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon . |
| 4,316,461 | 2/1982 | Marais ................ 128/DIG. 26 |
| 4,324,236 | 4/1982 | Gordon et al. . |
| 4,326,519 | 4/1982 | D'Alo et al. . |
| 4,362,156 | 12/1982 | Feller, Jr. et al. . |
| 4,392,853 | 7/1983 | Muto . |
| 4,397,647 | 8/1983 | Gordon . |
| 4,405,163 | 9/1983 | Voges et al. . |
| 4,449,975 | 5/1984 | Perry . |
| 4,453,933 | 6/1984 | Speaker . |
| 4,480,639 | 11/1984 | Peterson et al. . |
| 4,516,968 | 5/1985 | Marshall et al. . |
| 4,633,863 | 1/1987 | Filips et al. ................ 128/165 |
| 4,660,555 | 4/1987 | Payton . |
| 4,711,636 | 12/1987 | Bierman . |
| 4,742,824 | 5/1988 | Payton et al. . |
| 4,792,163 | 12/1988 | Kulle . |
| 4,795,429 | 1/1989 | Feldstein . |
| 4,826,486 | 5/1989 | Palsrok er al. . |
| 4,834,716 | 5/1989 | Ogle, II . |
| 4,852,844 | 8/1989 | Villaveces . |
| 4,857,058 | 8/1989 | Payton ................ 604/180 |
| 4,863,432 | 9/1989 | Kvalo . |
| 4,880,412 | 11/1989 | Weiss . |
| 4,897,082 | 1/1990 | Erskine . |
| 4,898,587 | 2/1990 | Mera . |
| 4,919,654 | 4/1990 | Kalt . |
| 4,934,375 | 6/1990 | Cole et al. . |
| 4,955,864 | 9/1990 | Hajduch . |
| 4,976,700 | 12/1990 | Tollini . |
| 4,981,469 | 1/1991 | Whitehouse et al. . |
| 4,997,421 | 3/1991 | Palsrok et al. . |
| 5,037,397 | 8/1991 | Kalt et al. . |
| 5,073,170 | 12/1991 | Schneider . |
| 5,084,026 | 1/1992 | Shapiro . |
| 5,135,506 | 8/1992 | Gentelia et al. . |
| 5,147,322 | 9/1992 | Bowen et al. . |
| 5,156,641 | 10/1992 | White . |
| 5,192,273 | 3/1993 | Bierman et al. . |
| 5,192,274 | 3/1993 | Bierman . |
| 5,344,414 | 9/1994 | Lopez et al. . |
| 5,354,282 | 10/1994 | Bierman ................ 604/174 |
| 5,380,293 | 1/1995 | Grant . |
| 5,380,294 | 1/1995 | Persson . |
| 5,382,239 | 1/1995 | Orr et al. . |
| 5,382,240 | 1/1995 | Lam . |
| 5,395,344 | 3/1995 | Beisang, III et al. . |
| 5,413,562 | 5/1995 | Swauger . |
| 5,443,460 | 8/1995 | Miklusek . |
| 5,456,671 | 10/1995 | Bierman . |
| 5,468,228 | 11/1995 | Gebert . |
| 5,468,230 | 11/1995 | Corn . |
| 5,484,420 | 1/1996 | Russo . |
| 5,496,282 | 3/1996 | Militzer et al. . |
| 5,496,283 | 3/1996 | Alexander . |
| 5,498,241 | 3/1996 | Fabozzi . |
| B1 5,147,322 | 1/1996 | Bowen et al. . |

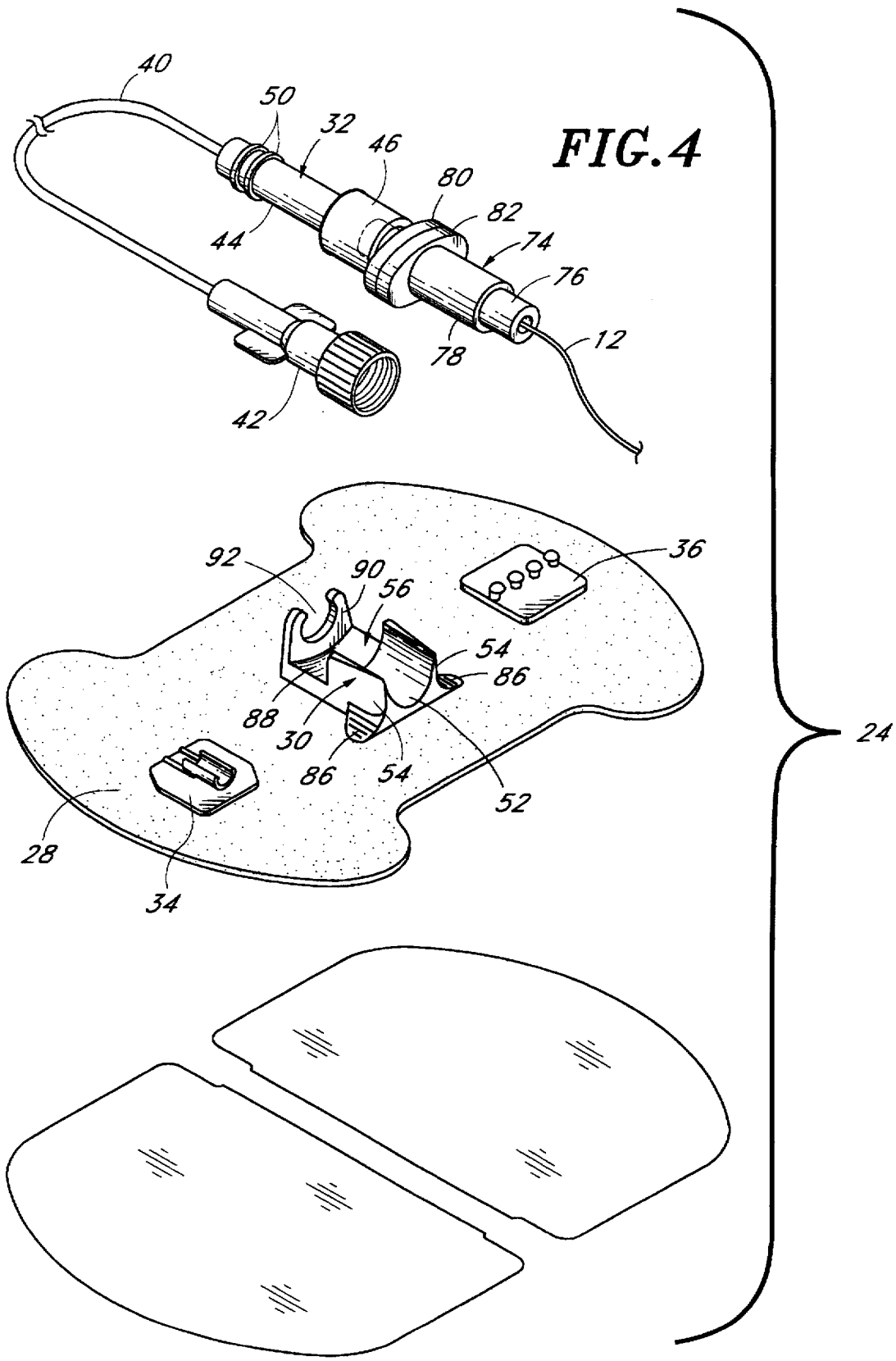

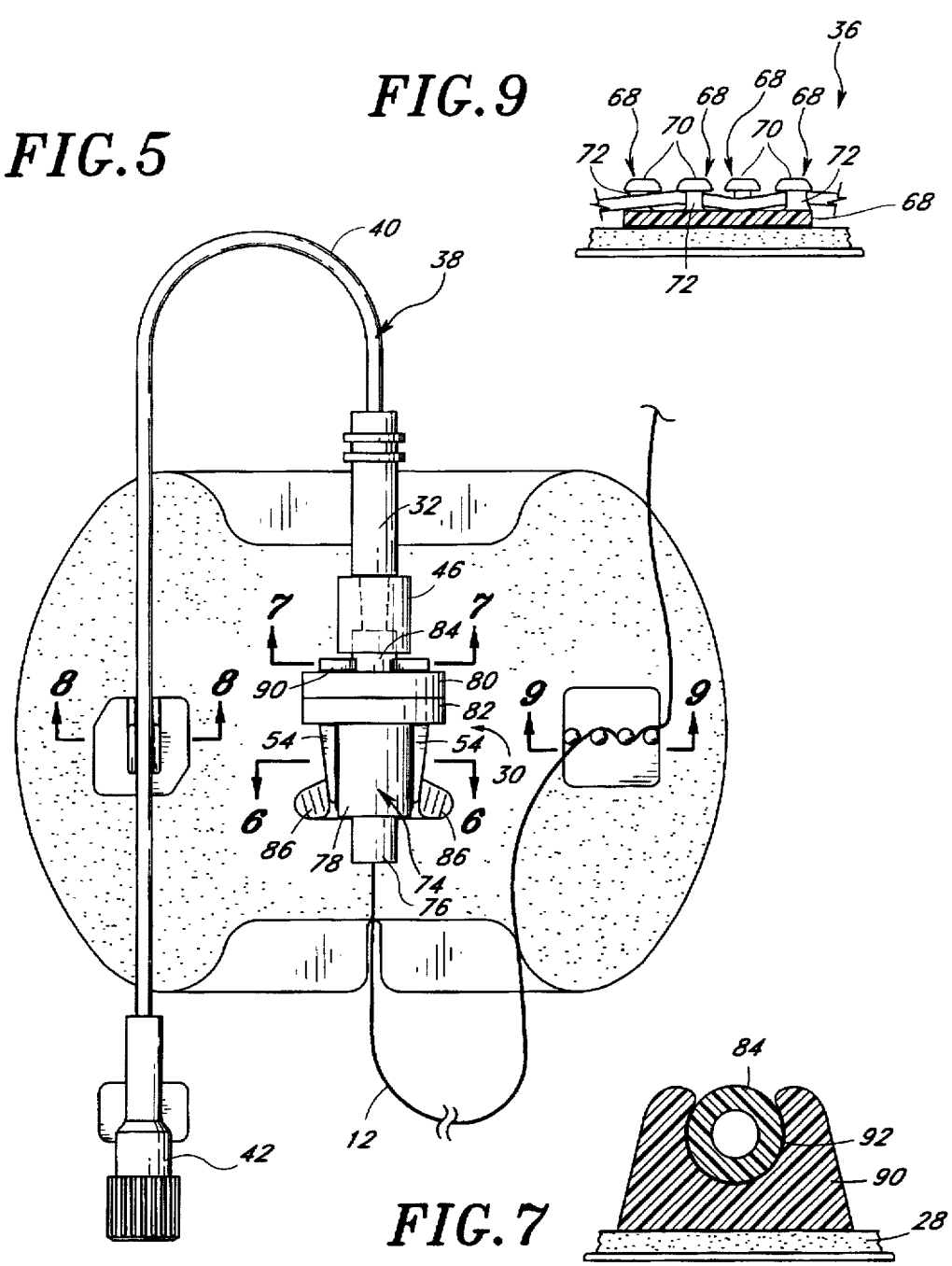
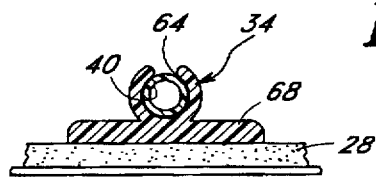
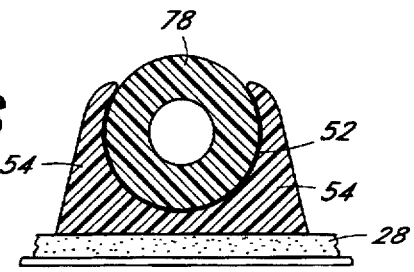

CATHETER ANCHORING SYSTEM AND METHOD OF USE

RELATED CASES

This application is a continuation-in-part of Ser. No. 08/223,948, filed Apr. 6, 1994, now U.S. Pat. No. 5,578,013, which is a continuation-in-part of Ser. No. 08/121,942, filed Sep. 15, 1993, now U.S. Pat. No. 5,456,671, which is a continuation-in-part of Ser. No. 08/034,340, filed Mar. 19, 1993 now U.S. Pat. No. 5,354,282.

BACKGROUND OF THE INVENTION

1. Field of the Invention

The present invention relates in general to percutaneous catheterization, and, in particular, to a device for and method of anchoring an indwelling epidural catheter proximal to an insertion site of the catheter.

2. Description of Related Art

Catheterization and delivery of anesthesia into the epidural space is commonly used to anesthetize a specific location on the patient. The anesthesia is typically a fluid that drains from a container positioned above the patient. An anesthesia delivery system delivers anesthesia to the epidural space. An infusion pump of the system pushes anesthesia through a fluid tube and into an epidural catheter. A conventional catheter adapter (e.g., Tuoghy-Borst connector) interconnects the fluid tube and the catheter. The distal end of the catheter is inserted into the epidural space to deliver anesthesia.

A health care provider (such as a nurse or anesthesiologist) often anchors the epidural catheter to the skin of the patient proximate to the insertion site using adhesive or surgical tape to maintain the position of the catheter while in use. Similarly, the connection between the fluid tube and the catheter is taped to the patient. A safety loop also is typically formed in the anchored section of the tube so that any tension applied to the tube will not pass directly to the catheter but will instead be absorbed by the slack in the safety loop, thus preventing discomfort to the patient or dislodgement of the catheter from the epidural space.

Taping to secure a catheter is undesirable for a number of reasons. The health care provider must waste valuable time applying the tape and often finds it awkward and frustrating to apply tape while wearing protective gloves; in March 1994, OSHA mandated health care providers to wear gloves when performing catheter securement and dressing change procedures. If the health care provider's gloves contact the adhesive of the tape, the integrity of the gloves often is impaired. In one study, over forty percent (40%) of glove pairs used with tape were found to contain holes of a sufficient size to allow blood borne pathogens to enter the glove. Contact with the adhesive of the tape thus produces a high incident of loss of barrier protection.

Patients also experience discomfort from taping and retaping when the catheter tube is replaced periodically (e.g., every 24 to 48 hr) to maintain sterility and free-flow of the fluid. Moreover, tape covering the catheter at the point of insertion must be removed to allow inspection of the insertion point for inflammation or infection and then replaced. Frequent application and reapplication of surgical tape can excoriate the patient's skin, increase patient discomfort and promote infections (e.g., meningitis).

In U.S. Pat. No. 5,192,273, U.S. Pat. No. 5,192,274 and U.S. Pat. No. 5,456,671, the present Applicant describes catheter anchoring systems that improve catheter stabilization and anchor. The present invention continues with this.

SUMMARY OF THE INVENTION

In accordance with one aspect of the present invention, an anchoring device includes a flexible anchoring pad having upper and lower surfaces. The lower surface is defined at least in part by an adhesive layer which releasably adheres to the patient's skin. The upper and lower surfaces together define an edge that includes a recess positioned about and axis that bifurcates the recess. A clip, which is a device for releasably retaining, grasping, gripping or securing a portion of another element of the system, includes a plurality of channels to receive a section of the flexible tubular body of the catheter. The channels are supported by the anchor pad and are arranged relative to the recess such that a portion of the received catheter body section lies generally transverse to or across the axis defined by the alignment of the channels.

Another aspect of the present invention involves a catheter anchoring device for securing an in-dwelling catheter proximate to a point of insertion of the catheter into a body lumen of the patient. The anchoring device includes a flexible the pad having an adhesive layer which releasably adheres to the patient's skin. The anchor pad includes a recess positioned on an edge. Means for inhibiting movement of a section of the catheter body relative to the anchor pad is provided. The means are attached to the anchor pad and are positioned to generally align with a center line of the anchor pad recess.

An additional aspect of the present invention involves a catheterization kit comprising a first anchoring device for securing a catheter connected to a fluid tube and second anchoring device for securing the catheter proximate to the insertion site of the catheter. The first catheter anchoring device includes a flexible anchor pad having an adhesive surface which releasably adheres to the patient's skin. The anchor pad supports a cradle which receives a catheter adapter. The catheter adapter is configured to interconnect a tube with the catheter. The second catheter anchoring device includes a flexible anchor pad having an adhesive surface which releasably adheres to the patient's skin. A clip includes a plurality of channels to receive a section of a flexible tubular body of the catheter. The channels are arranged on the anchor pad to give the received catheter body section a serpentine shape. The anchor pad supports the clip.

A preferred method of securing an in-dwelling catheter within a body lumen proximate to a insertion point of the catheter involves providing a flexible anchor pad which includes an adhesive layer. The adhesive layer releasably attaches to the patient's skin. The anchor pad also supports a clip which is configured to receive a section of the catheter body such that at least a portion of the catheter body lies generally transverse to a center line of a recessed portion of the anchoring pad. The anchoring pad is positioned proximate to the point of insertion of the catheter. A section of the catheter body is threaded through the clip and a flexible anchor pad is applied to the patient's skin proximate to the point of insertion on the catheter.

In accordance with a method of securing an in-dwelling epidural catheter to the body of a patient involves providing a first anchor pad that has an adhesive surface which releasably attaches to the patient's skin. The anchor pad also supports a retainer for holding a catheter adapter body. A second anchor pad also is provided. The second anchor pad has an adhesive surface which releasably attaches to the patient's skin and supports a clip for receiving a flexible tubular portion of the catheter. The clip has a plurality of channels which receives a portion of the flexible catheter body. The channels are arranged on a base of the clip to give the received flexible catheter body a serpentine shape with a catheter body inserted in adjacent channels. The second anchor pad is positioned proximate to the point of insertion of the epidural catheter. A portion of the catheter body is threaded through the channels of the clip of the second anchor pad such that the threaded portion generally has a serpentine shape. The second anchor pad is applied to the patient's skin proximate to the point of insertion of the epidural catheter by pressing the adhesive surface onto the patient's skin. The catheter is extended to a position on the patient's body away from the point of insertion of the epidural catheter. The catheter is attached to the catheter adapter and a fluid supply tube is also attached to the catheter adapter. The catheter adapter is placed into a retainer on the first anchor pad and the first anchor pad is applied to the patient's skin at a position distant from the point of insertion of the epidural catheter. This is accomplished by pressing the adhesive surface to the patient's skin.

It should be understood that both the foregoing general description and the following detailed description are exemplary and explanatory only and are not restrictive of the invention as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 1A illustrates a first anchoring device of the system holding an epidural catheter and adaptor interconnection for connecting to a fluid supply tube attached to the front side of the patient's body on the abdomen with the catheter extending around the patient's waist to the back side of the body. The phantom lines of FIG. 1A show the anchor pad with the epidural catheter and adaptor interconnection attached to the patient's chest with the catheter extending over the patient's shoulder.

FIG. 1B shows a second anchoring device of the system attached to the patient's body near to the insertion site of the catheter into the patient's epidural space. The catheter passes around the patient's body from the front to the rear (around the waist or, as shown in phantom lines, over the shoulder) and is looped through a clip of the catheter anchoring device.

FIG. 4 is an exploded top perspective view of the first anchoring device of FIG. 3.

FIG. 5 is a plan view of the first anchoring device shown in FIG. 3.

FIG. 6 is a cross-sectional view of a retainer of the first anchoring device of FIG. 5 taken along line 6—6.

FIG. 7 is a cross-sectional view of the retainer of FIG. 5 taken along line 7—7.

FIG. 8 is a cross-sectional view of a tube clip of the first anchoring device of FIG. 5 taken along line 8—8.

FIG. 9 is a cross-sectional view of a catheter clip of the first anchoring device of FIG. 5 taken along line 9—9 of FIG. 3.

DETAILED DESCRIPTION OF PREFERRED EMBODIMENTS

Figure 1:
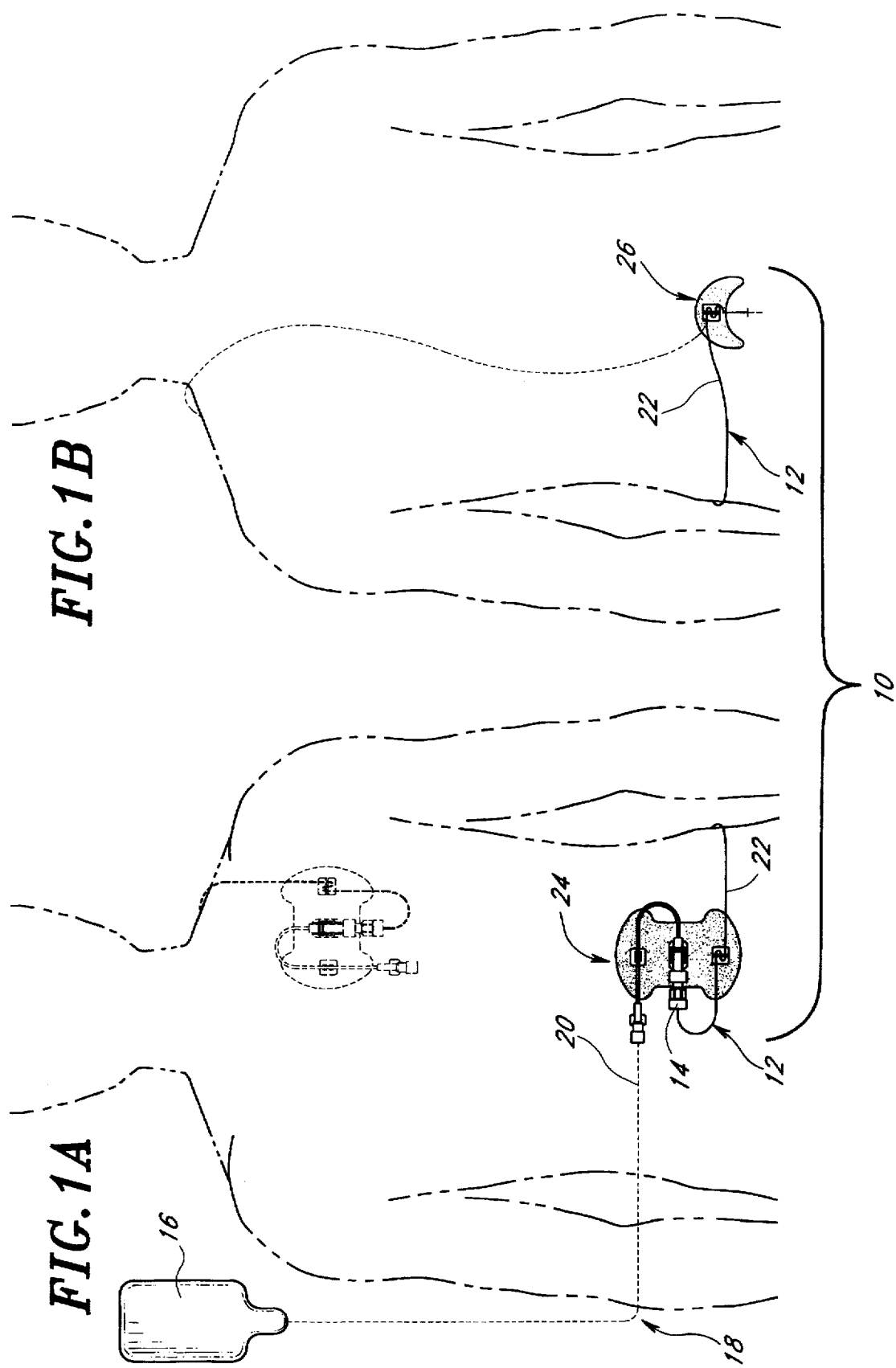
FIGS. 1A and 1B together show the catheter anchoring system in place on a patient's body.

FIGS. 1A and 1B together illustrate an epidural catheter anchoring system 10 in accordance with a preferred embodiment of the present invention. Although the following description describes the present anchoring system 10 in connection with an epidural catheter 12, the anchoring system 10 can be used with other types of catheters or small-bore and micro-bore tube. The description of the present anchoring system 10 in conjunction with an epidural catheter 12 therefore is merely exemplary, and is not intended to limit the scope of the following claims in any way.

Before describing the present catheter anchoring system 10, an exemplary epidural catheter 10 will first be described in general terms to assist the reader in understanding the interconnection between the catheter 12 and the anchoring system 10. The proximal end of the catheter includes a conventional Tuoghy-Borst connector 14 carrying an external thread. As used herein, the terms "proximal" and "distal" are in reference to a fluid supply container 16 (see FIG. 1A) at an upstream end of a fluid delivery system 18, and will be used to designate comparative locations along the fluid flow stream through the fluid delivery system 18 and the catheter 12. The Tuoghy-Borst connector 14 is adapted to be coupled to a fluid supply tube 20 (schematically illustrated in FIG. 1A) of a fluid delivery system 18 by the anchoring system 10, as described below.

A flexible tubular catheter body 22 extends from the Tuoghy-Borst connector 14 and terminates in a distal end (i.e., downstream end). The distal end of the catheter body 22 is designed to be inserted through the dura membrane and left indwelling within the epidural space at a desired location.

As seen in FIG. 1, the anchoring system 10 desirably includes a first anchoring device 24 and a second anchoring device 26 which together secure a catheter 12 to the patient's body at two locations. The first anchoring device 24 secures the proximal end of the catheter 12 to the patient, while the second anchoring device 26 secures a near-distal portion of the catheter body 22 to the patient. A portion of the first anchoring device 24 connects a fluid supply tube 20 of the fluid delivery system 18 to the catheter 12, as described below.

The first anchoring device 24 desirably is attached to the front of the patient's torso on the abdomen or on the chest (as shown in phantom lines in FIG. 1A) to allow easy access by the health care provider. This location also is more comfortable to the patient when lying on his or her back. Although the first anchoring device 24 desirably is attached to the front side of the torso, it can in the alternative be attached to the patient's back or side in closer proximity to the second anchoring device. And, as seen in FIG. 1B, a near-distal portion of the catheter body 22 is secured to the second anchoring device 26 proximate to the point of catheter insertion.

This dual-location anchoring system improves patient comfort and reduces catheter migration and dislodgement, as explained below. The anchoring system 10 also securely anchors the catheter 12 to the patient without the use of surgical tape, thereby adding to the health care provider's efficiency and reducing the patient's discomfort. The individual components of the first and second anchoring devices 24, 26 will now be described in detail.

First Anchoring Device

Figure 2:
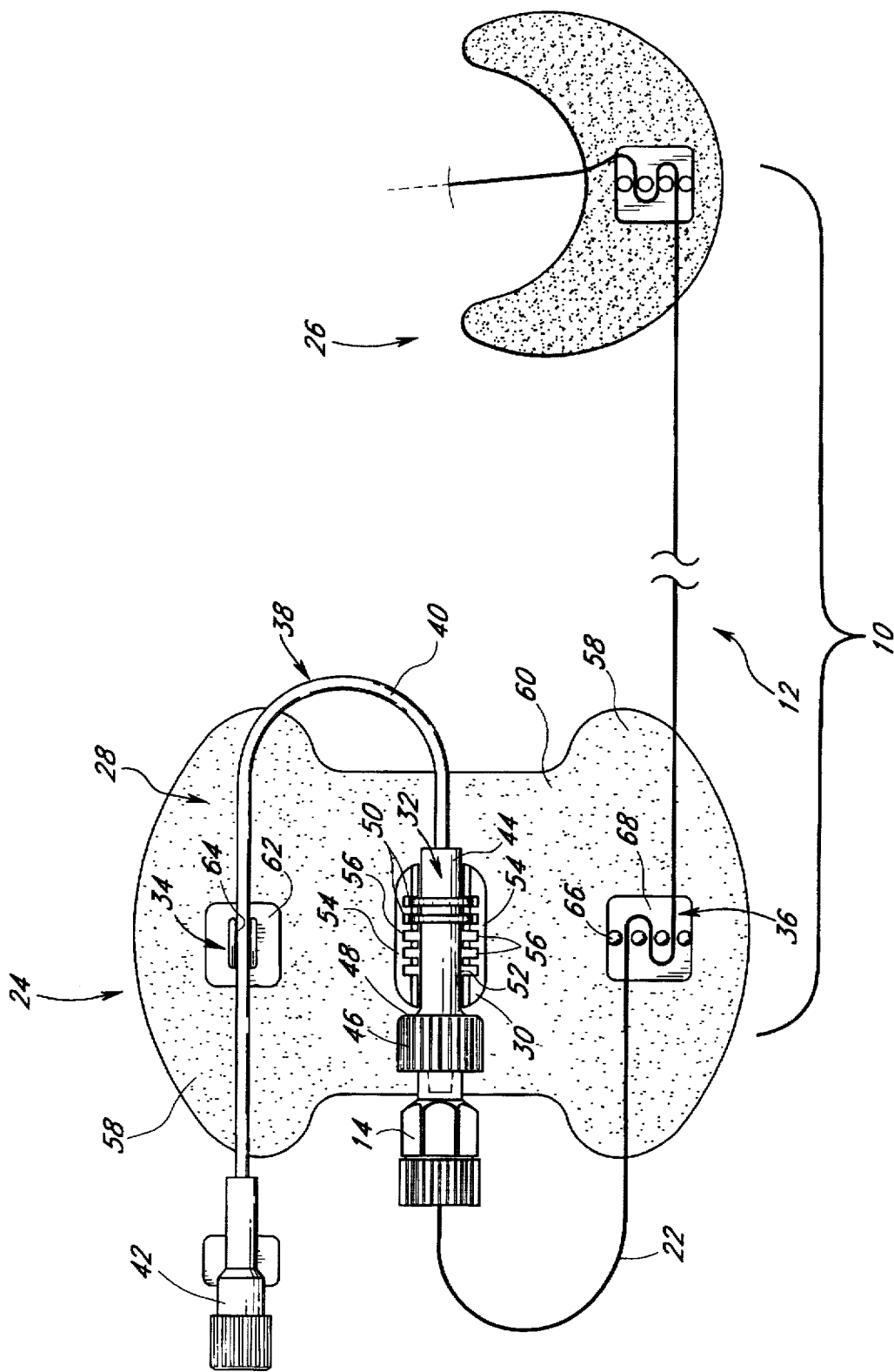
FIG. 2 is an enlarged top plan view of the second anchoring system of FIGS. 1A and 1B.

With reference to FIG. 2, the first anchoring device 24 includes an anchor pad 28 which supports a cradle or retainer 30. The retainer 30 is designed to releasably receive and to secure a catheter adaptor 32 or the proximal end of the catheter 12 itself to the anchor pad 28. The anchor pad 28 in turn is adhered to the patient's skin. The catheter adaptor 32 couples the catheter 12 to the fluid supply tube 20 (FIG. 1A). The first anchoring device 24 also desirably includes a tube clip 34 and a catheter clip 36 to form safety loops in the tube and the catheter 12 and to further secure the tube and catheter 12 to the anchor pad 28.

The first anchoring device 24 can take a variety of forms and include any of a number of catheter adaptor types which will be well known to those in the art. For instance, the first anchoring device 24 can be configured in accordance with the disclosures of U.S. Pat. Nos. 5,354,282 and 5,456,671, and the disclosure of copending application Ser. No. 08/223,948, filed on Apr. 6, 1994. These prior cases have all been filed in the name of the present applicant, Steven F. Bierman, and assigned to the assignee hereof, and are hereby incorporated by reference.

The first anchoring device 24 also can be configured in accordance with the disclosure of copending application Ser. No. 08/601,527, filed Feb. 14, 1996, which is hereby incorporated by reference. FIGS. 3–9 illustrates this additional embodiment of the first anchoring device. The following description will first describe the first anchoring device 24 in accordance with the embodiment of FIGS. 1 and 2. The other illustrated embodiment of the first anchoring device 24 will then be described in connection with FIGS. 3–9. It should be understood, however, that either of the illustrated embodiments of the first anchoring device 24, as well as other similar types of anchoring devices, can be used equally as well with the present catheter anchoring system 10. Those skilled in the art will be readily able to select an appropriate type of first anchoring device 24 depending upon the particular procedure or application, as well as upon the particular catheter 12 to be secured.

Extension Set

With reference to FIG. 2, the first anchoring device 24 includes an extension set 38 to connect together the catheter 12 and the fluid supply tube 20 (FIG. 1A). The extension set 38 comprises the catheter adaptor 32 and a tube segment 40 attached to the proximal end of the adaptor 32. The tube segment 40 terminates at its proximal end at a conventional tube connector 42 (e.g., a lure-lock connector). The connector 42 is coupled to a corresponding connector on the distal end of the fluid tube 20 of the fluid delivery system 18. The connectors cooperate to interconnect the tube segment 40 and the fluid tube 20. If desired or necessary, a filter (not shown) may be attached between the connector on the proximal end of the extension set 38 and the fluid supply tube 20, as described below.

Catheter Adaptor

In the illustrated embodiment, the catheter adaptor 32 includes a tubular body 44 defined between a distal end and a proximal end of the body 44. The proximal end of the adaptor body 44 is permanently attached to a distal end of the tube segment 40 of the extension set 38.

The distal end is configured to engage a proximal end of the catheter 12. Although FIGS. 1 and 2 illustrate the distal end of the adaptor 32 as having a frusto-conical shape configured to engage a standard Tuoghy-Borst connector or lure-lock type catheter hub, it is contemplated that the distal end could be configured as well to engage other types of connectors.

In the illustrated embodiment, the catheter adaptor 32 includes a standard lure-lock type fitting 46 attached to the body 44 of the catheter adaptor 32 so as to circumscribe the distal end of the catheter adaptor 32. The lure-lock fitting 46 preferably is attached in a manner which permits the fitting 46 to be rotated about the catheter adaptor body 44. It is contemplated, however, that the distal end of the adaptor 32 could comprise a female lure-lock type connector (i.e., a hub including nubs or threads on its external surface) as well if required by a particular application.

With reference to FIG. 2, the lure-lock fitting 46 has a generally tubular shape with a closed proximal end 48. The closed end includes an aperture of a sufficient size to receive a portion of the adaptor body 44, as described below. The fitting 46 includes conventional internal threads in order to engage corresponding external threads on the Tuoghy-Borst connector 14, as described above.

The adaptor body 44 includes an annular groove (not shown) which receives a portion of the closed end 48 of the lure-lock fitting 46 to interconnect the fitting 46 and the adaptor body 44. This interconnection also permits the fitting 46 to be rotated about the adaptor body 44.

To assemble the catheter adaptor 32, the conical shaped distal end of the body 44 is inserted into the aperture of fitting's closed end 48. The body 44 is then forced into the fitting to slightly deflect the closed end 48 until the closed end 48 snaps into the annular groove of the body 44. In this position, the body 44 captures a portion of the fitting 48 to couple these elements together.

The adaptor 32 also includes at least one annular collar 50 interposed between the proximal and distal ends of the tubular body 44. In the illustrated embodiment, the adaptor 32 includes two annular collars 50 which lie toward the proximal end of the tubular body 44.

Each annular collar 50 flares radially outwardly and circumscribes the tubular body 44. The annular collar 50 has a thickness measured in a longitudinal direction which is slightly less than a width of a slot in the retainer 30 so that the collar 50 fits within the slot of the retainer 30, as discussed in detail below. The spacing between the collars 50 also equal the spacing between the slots on the retainer 30.

The adaptor 32 is preferably formed of a durable, biocompatible plastic material. The adaptor 32 more preferably is formed of clear plastic so a nurse can see bubbles or back-flow through the adaptor. In an exemplary embodiment, the adaptor 32 is formed of polycarbonate by injection molded; however, those skilled in the art will readily appreciate that the adaptor 32 can be formed by other construction methods known in the art.

Retainer

In the illustrated embodiment of FIG. 2, the retainer 30, which cooperates with the catheter adaptor 32, includes a central channel 52 interposed between a pair of opposing longitudinal walls 54. The retainer 30 includes a flat base which is attached to an upper surface of the anchor pad 28. The central channel 52 extends through the retainer 30 along an axis that is generally parallel to a longitudinal axis of the retainer 30.

In the illustrated embodiment, the central channel 52 has a generally circular cross-sectional shape that is truncated at an upper end to form an opening. The central channel 52 in cross-section extends through an arc greater than 180° about the channel axis such that the lateral length of the opening at the upper end is less than the diameter of the central channel 52. The diameter of the central channel 52 is sized to receive the tubular body 44 of the catheter adaptor 32. Preferably, the diameter of the central channel 52 generally matches the outer diameter of the tubular body 44.

The longitudinal walls 54 of the retainer 30 are substantially identical and form a uniform series of slots 56. Each wall 54 comprises at least one slot 56, and preferably comprises between one and ten slots 56. In the exemplary embodiment shown in FIG. 2, the walls 54 comprise a series of five slots 56. Each slot 56 is sized in width to receive the annular collar 50 of the adaptor body 44 to prevent displacement of the adaptor 32 along the axis of the central channel 52 of the retainer 30. Each slot 56 has a generally rectangular shape and extends from the exterior surface of the retainer 30 through the wall 54 and into the central channel 52. Each slot 56 also extends from the upper edge of the wall 54 to a point below the bottom of the central channel 52. The height of the slot 50 is greater than the distance between the upper edge and the bottom of the central channel 52 of the retainer 30. Opposing slots 56 on opposite sides of the central channel 52 form a lateral groove (not shown) which receive the collar 50 of the adaptor body 44.

The retainer 30 is made of a somewhat flexible but relatively stiff plastic material to allow the adaptor 32 to force between the upper edges of the longitudinal walls 54 when the adaptor 32 is pressed into the central channel 52 of the retainer 30. Thus, once the retainer 30 is within the central channel 52, the longitudinal walls 54 snap inwardly to their normal position so that the adaptor body 44 is held within the retainer 30. For example, the retainer 30 may be formed of injection molded polycarbonate although those skilled in the art will appreciate that other materials such as polyvinylchloride, polypropylene, polyurethane, tetrafluoroethylene (e.g., TEFLON®), polytetrafluoroethylene (PTEF), acetal resin (e.g., DELRIN®), chlorotrifluoroethylene (e.g., KEL-F®), nylon or like polymers, and other methods of manufacture may be used.

The retainer or cradle, however, can have other shapes in order to retain a portion of the catheter hub, Tuoghy-Borst connector or catheter adaptor. For instance, the retainer can receive a portion of the catheter adaptor in a relief, recess, depression, caged space, groove, or similar semi-enclosed space, and maintain it in the space by a releasable clamp or similar locking mechanism.

With reference to FIG. 2, the retainer 30 desirably is secured to the anchor pad 28 by means of a light-activated adhesive, cyanoacrylate, or other bonding material. A UV-activated, pressure-sensitive adhesive desirably secures the retainer 30 to the upper surface of the anchor pad 28. In the alternative, the retainer 30 can be embedded or woven into the anchor pad 28.

Anchor Pad

The flexible anchor pad 28 comprises a layer of closed-cell polyethylene form and a bottom adhesive mono-layer of medical-grade adhesive. The adhesive can be either diaphoretic or nondiaphoretic, depending upon the particular application. The foam layer with adhesive bottom layer is available commercially from New Dimensions in Medicine of Columbus, Ohio. An upper surface of the foam layer is energized by corona treating the foam with a low electric charge, as known in the art. The corona-treated upper surface of the anchor pad 28 improves adhesive (other types of adhesive or bonding materials) adhesion (i.e., adhesive qualities) when attaching the retainer 30 to the anchor pad 28.

A removable paper or plastic backing (not shown) desirably covers the bottom adhesive surface before use. In the illustrated embodiment, a siliconized paper is used as the release layer. The backing preferably resists tearing and is divided into a plurality of pieces to ease attachment of the pad to the patient's skin. The backing desirably is split along a center line of the flexible anchor pad 28 in order to expose only half of the adhesive bottom surface at one time. The backing also advantageously extends beyond at least one edge of the anchor pad 28 to ease removal of the backing from the adhesive layer.

In the illustrated embodiment, as best seen in FIG. 2, the anchor pad 28 includes a pair of lateral wing sections 58 which extend from a narrowed center section 60 of the anchor pad 28. The lateral ends 58 of the anchor pad 28 have more contact area to provide greater stability and adhesion to the patient's skin.

The retainer 30 is positioned on the narrowed center section 60 of the anchor pad 28 with its longitudinal axis lying generally transverse to a longitudinal axis of the narrowed center section 60. The longitudinal axis of the retainer 30 also desirably aligns with the split line of the release layer. In this manner, the health care provider can use the split line or an edge of one of the release layer pieces which forms the split line to align the position of the retainer 30 relative to the axis of the catheter 12 exiting the insertion site.

The anchor pad 28 also may include indicia (not shown) which further indicates the proper orientation of the anchor pad 28 in reference to the catheterized cite. Such indicia can include, for example, arrows, words, icons, or other graphics.

Tube Clip

As seen in FIG. 2, the anchor pad 28 desirably supports the tube clip 34 for retaining a portion of tube segment 40 of the extension set 38. As used herein, a "clip" means a device for releasably retaining, grasping, gripping or securing a portion of another element of the system, such as, for example, a portion of the tube segment 40 or the catheter body 22. Although in the embodiment of FIG. 2 the first anchoring device 24 includes a single tube clip 34, it will be appreciated by those skilled in the art that the first anchoring device 24 can include multiple tube clips 34 attached at a variety of locations on the anchor pad 28.

In the illustrated embodiment, the tube clip 34 includes a flat base 62 which is adhered to or is embedded or woven into the anchor pad 28. The tube clip 34 also defines a central channel 64 having a generally circular cross-section configuration truncated at the top to form an upper orifice into which the tube segment 40 is inserted by positioning the tube segment 40 over the orifice and pressing downwardly on the fluid tube 40 or gently pulling the tubing 40 across the orifice. The diameter of the central channel 64 of the tube clip 34 is preferably slightly less than that of the tube segment 40 of the extension set 38 to ensure a secure interconnection when the tube segment 40 is inserted into the tube clip 34.

The upper edge of the central channel 64 is preferably tapered to form a smooth rounded transition between the central channel 64 and the upper edge. Moreover, tapered rounded ends are also preferred at the proximal and distal ends of the clip 34. Tapered ends help to guide the tube segment 40 into the central channel 64 when the tubing 40 is pressed or gently pulled into the central channel 64 thus eliminating the need to pinch the tube 40 to insert it into the central channel 64 of the tube clip 34. Thus, when in use, the upper edge between the proximal and distal ends of the clip 34 has a self-guiding aspect for insertion of the tube segment 40 into the central channel 64 when the tubing 40 is drawn across the upper edge.

The tube clip 34 is preferably made of a relatively stiff plastic material (e.g., polycarbonate). Those skilled in the art will know that the tube clip 34 can be made by a variety of methods using a variety of materials such as, for example, polycarbonate, polyvinylchloride, polypropylene, polyurethane, tetrafluoroethylene (e.g., TEFLON®), poly-tetrafluoroethylene (PTEF), acetal resin (e.g., DELRIN®), chlorotrifluoroethylene (e.g., KEL-F®), nylon or other polymers.

Catheter Clip

The catheter clip 36 of the first anchor device 24 secures the epidural catheter body 22 to the anchor pad 28 by snaking the catheter body 22 through a series of retainers 66 to form an S-curve in the catheter body 22. Although not illustrated, the first anchoring device 24 can include several catheter clips 36 in order to suit a particular application.

The catheter clip 36 includes a base plate 68 which is adhered to the upper surface of the anchor pad 28 or embedded or woven into the anchor pad 28. The base plate 68 supports a plurality of upright retainers 66.

With reference to FIG. 9, each retainer 66 has a generally expanded head 70 and a generally cylindrical stem 72 supporting the head 70. (FIG. 9 illustrates an identical catheter clip 36 used in connection with another embodiment of the first anchoring device 24 described below.) The stems 72 of the upright retainers 66 extend upwardly from the base plate 68.

The retainer stems 72 are positioned apart from one another by a distance slightly greater than the diameter of the epidural catheter body 22. The expanded heads 70 of the retainers 66, however, lie adjacent to one another, being spaced apart by a distance slightly less than the diameter of the catheter body 22. Thus, the base 68 and each pair of adjacent stems 72 and expanded heads 70 form a channel having a generally elliptical cross-sectional shape with an orifice at the top of the channel between the adjacent heads 70. The catheter body 22 can be snaked through adjacent stems 72 and maintained in the elliptical channel by the expanded heads 70 to prevent the catheter body 22 from disengaging from the catheter clip 36.

The catheter clip 36 desirably includes at least two channels to allow a health care provider to snake the catheter body 22 back and forth through the channels to capture the catheter body 22 within the clip 36. In the illustrated embodiment, the catheter clip 36 desirably includes at least four retainers 66 which allows the catheter body 22 to be snaked back and forth through at least three channels to give the catheter body 22 a serpentine shape as it passes through the channels. The changes in the direction of the catheter body 22 through the clip 36 inhibits movement of the catheter in a direction along its length (i.e., in the axial or longitudinal direction). It will be appreciated by those skilled in the art that the number of retainers 66 may be increased to form additional channels to allow create additional directional changes of the portion of the catheter 12 passing through the clip 36 to further improve the securement provided by the catheter clip 36.

As best understood from FIG. 9, the outer or end retainers 66 of the catheter clip 36 desirably have enlarged stem portions. The enlarged head 70 overhangs the stem 72 only to a side adjacent another retainer 66. This configuration strengthen the clip 36 and eliminate sharp exterior edges on the clip 36.

The catheter clip 36 may be manufactured in a variety of ways using a variety of materials that are durable, flexible, relatively stiff and preferably inert and non-toxic, using methods well known in the art. Preferably the catheter clip 36 is integrally formed of injection-molded plastic or polymer material such as, for example, polycarbonate, polyvinylchloride, polypropylene, polyurethane, tetrafluoroethylene (e.g., TEFLON®), polytetrafluoroethylene (PTEF), acetal resin (e.g., DELRIN®), chlorotrifluoroethylene (e.g., KEL-F®), nylon or other polymers.

Additional Embodiment of First Anchoring Device

FIGS. 3–9 illustrate another embodiment of the first anchoring device 24 which can be used with the present anchoring system 10. The retainer 30 of this embodiment takes different forms from that described above in connection with the embodiment of the first anchoring device 24 illustrated in FIGS. 1 and 2; however, the anchor pad 28, tube clip 34, and catheter clip 36 and extension set 38 (including the catheter adaptor) are substantially identical, and therefore the above-description will apply equally to these components of this embodiment, unless noted to the contrary. For ease of understanding, like reference numerals will be used to designate like parts of the two embodiments.

Figure 3:
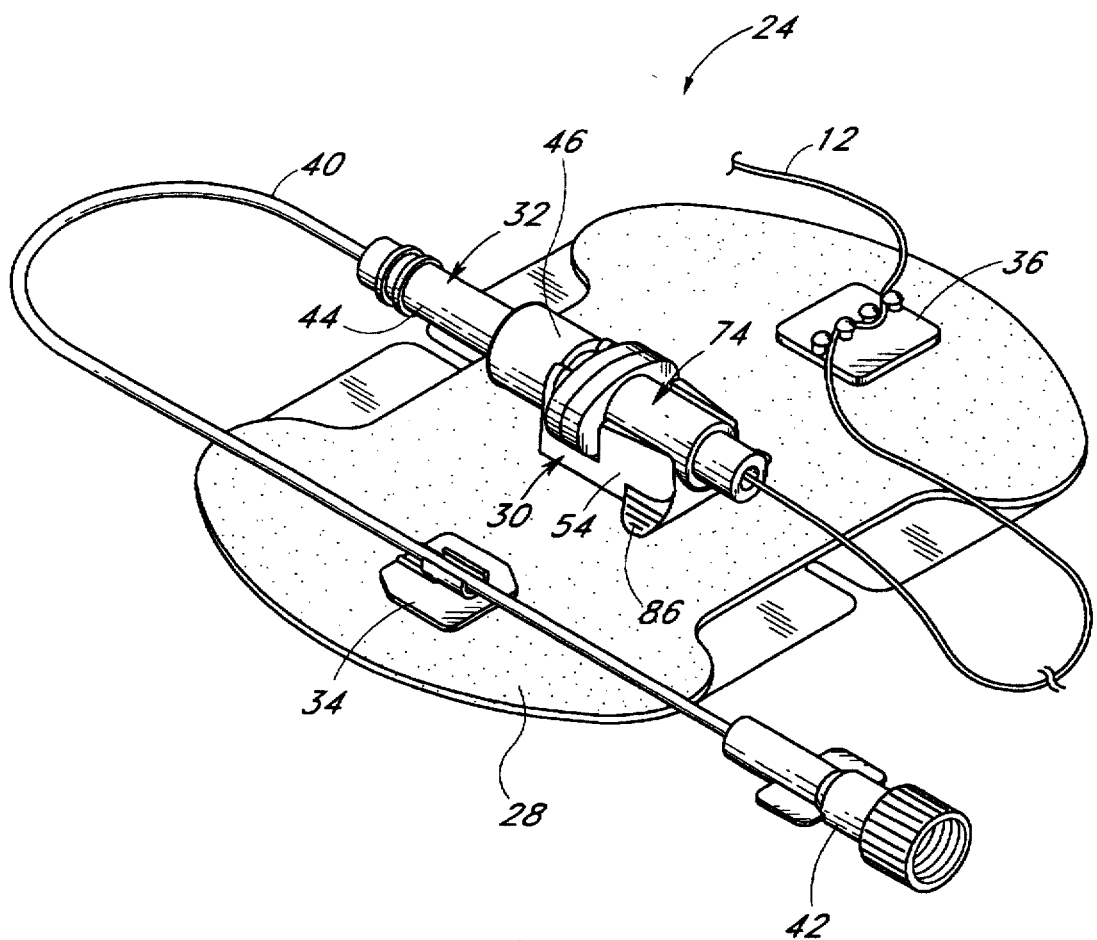
FIG. 3 is a top perspective view of the first anchoring device configured in accordance with another preferred embodiment of the present invention.

With reference to FIG. 3, the illustrated catheter retainer is adapted to receive a catheter fitting which is used in place of the Tuoghy-Borst connector. In the illustrated embodiment the catheter fitting 74 is available commercially under the trademark SNAP-LOCK™ from Arrow International of Reading, Pa. The catheter fitting 74 securely connects the extension set 38 to the catheter 12. The catheter 12 is releasably connected to the fitting 74 by threading a proximal end of the catheter 12 through a central channel (not shown) within the fitting 74. The central channel passes through a collet 76 of the fitting 74. An outer ring member 78 is slid over the collet section 76 to secure and seal the catheter within the central channel. The ring member 78 is slide toward a collar 80 on the fitting body until a collar 82 on the ring member 78 contacts the body collar 82. As seen in FIG. 4, the collars 80, 82 generally have identical elliptical shapes and sizes, and rest flush against each other with the ring member 78 compressing the collet 76. Friction between the collet 76 and the ring member 78 maintains the ring member 78 in this position.

The catheter fitting 74 generally presents a cylindrical shape on the distal side of the abutting collars 82, 80. A tubular portion of the ring member 78 principally defines this cylindrical shape.

The catheter fitting 74 also includes a threaded lure-lock connector. The connector cooperates with a corresponding connector on the end of the catheter adaptor 32. As understood from FIG. 5, a gap 84 typically exists between the engaged connectors and the proximal side of the adaptor collar 80. The exposed portion 84 of the fitting 74 has a tubular shape of a diameter smaller than the diameter of the tubular portion of the ring member 78.

The retainer 30 is configured to receive and secure in place the catheter fitting 74. For this purpose, as seen in FIG. 4, the retainer 30 includes a large central channel 52 interposed between a pair of opposing longitudinal wall 54. The central channel 52 is sized to receive the tubular portion of the fitting ring member 78. The central channel 52 extends along an axis which is generally collinear to the longitudinal axis of the retainer 30.

As best seen in FIGS. 4 and 6, the central channel 52 has a generally circular cross-sectional shape which is truncated at an upper end to form a generally C-shaped channel having an upper opening. The central channel 52 has a diameter sized to receive the generally tubular portion of the tube fitting ring member 78. In a preferred embodiment, the diameter of the central channel 52 generally matches that of the tubular portion or is slightly larger.

In cross-section, as seen in FIG. 6, the central channel 52 extends through an arc which is greater than 180° about the channel axis such that the lateral width of the opening is less than the diameter of the central channel 52. In an exemplary embodiment, the central channel 52 extends through an arc of about 200° about the channel axis.

The longitudinal walls 54 are substantially identical. The length of each wall 54, measured in the longitudinal direction, is preferably coextensive with the length of the tubular portion of the adaptor ring member 78.

The walls 54 desirably have a minimum thickness at the top of the channel 52 to allow flexure of the top portions of longitudinal walls 54 away from each other. The retainer 30 further is formed of rigid but flexible material to permit this deflection of the walls 54 when inserting and removing the tubular portion 78 of the catheter fitting 74 from the channel 52. Although the retainer 30 can be formed of any of a wide variety of materials, the retainer 30 desirably is formed of polycarbonate or a like polymer, as discussed below.

As best seen in FIG. 5, the walls 54 desirably give the retainer 30 a width in the lateral direction which is less than the common maximum width of the adaptor collars 80, 82. The distal ends of the longitudinal walls 54 taper in thickness to reduce the width of the retainer 30 at this end.

At the distal end of the retainer 30, a finger platform 86 extends from each wall. The platforms 86 have a sufficient size to allow the tips of the health care provider's index finger and thumb to press against the platforms 86. In this manner, the health care provider can press the retainer 30 against the patient when removing the catheter fitting 74 from the retainer.

As best seen in FIG. 4, at least one lateral slot 56 extends through the retainer 30 in a direction that is generally perpendicular to the axis of the retainer 30. The slot 56 is sized to receive the collars 80, 82 of the catheter fitting 74 and includes an arcuate bottom surface 88. The bottom surface 88 is shaped to match the section of the elliptical shaped collars 80, 82 that sit against the bottom surface 88 with the catheter fitting 74 positioned within the retainer 30.

The slot 56 extends through the walls 54 of the retainer 30 such that the ends of the elliptical collars 80, 82 of the catheter fitting 74 are exposed on either side of the retainer 30. That is, the width of the retainer 30 at the location of the slot 56 is less than the major diameter of the elliptical shaped collars 80, 82 of the catheter fitting 74.

The thickness of the slot 56, as measured in the longitudinal direction, generally matches the thickness of the abutting collars 80, 82, measured in the same direction. In this matter, the slot 56 captures a portion of the ends of the collars 80, 82 to prevent longitudinal movement of the catheter fitting 74 within the retainer 30.

As best seen in FIG. 6, the slot 56 has a height, which is measured in the transverse direction, between an upper edge of the longitudinal wall 54 and the bottom 88 of the slot 56. The bottom 88 extends below the central channel 52 in order to receive the portion of the catheter fitting collars 80, 82 that extend below the tubular portion of the ring member 78.

With reference to FIGS. 4 and 5, the retainer 30 includes a slender front wall 90 positioned on the proximal side of the slot 56. The thickness of the wall 90 as measured in the longitudinal direction desirably is less than the gap 84 formed between the catheter fitting collar 80 and the lure-lock connector when engage with the adaptor 32.

As best seen in FIGS. 4 and 7, the front wall 90 defines a second channel or aperture 92 which receives the proximal tubular portion 84 of the fitting 74. (In order to differentiate between the proximal and distal channels of the retainer, the following discussion will refer to the channel in the front wall as an aperture; this is done without limiting the invention.) The aperture 92 generally has a circular shape which is truncated at an upper end so as to define an upper opening to the aperture 92. The center of the circular shape of the aperture 92 generally lies on the axis of retainer 30.

The aperture 92 has a diameter sized to receive the proximal tubular portion 84 of the fitting 74. In a preferred embodiment, the diameter of the aperture 92 generally matches that of the proximal tubular portion 84 or is slightly larger.

The aperture 92 desirably extends through an arc which is greater than 180° about the retainer axis such that the lateral width of the opening is less than the diameter of the aperture 92. In an exemplary embodiment, the aperture 92 extends through an arc of about 200° about the retainer axis.

As seen in FIG. 7, the upper edges of the front wall 90 proximate to the aperture 92 opening are rounded and slop toward the opening. This configuration helps guide the tubular portion 84 of the catheter fitting 74 into the aperture 92. It also helps deflect the upper ends of the front wall 90 in the lateral direction to allow the health care provider to push the tubular portion 84 into the aperture 92.

The circular portion of the aperture 92, however, intersects with each slopped upper edge at a generally sharp angle. The resulting distinct transition point inhibits unintentional retraction of the fitting tubular portion 84 from the aperture 92.

The retainer 30 may be constructed in any of a variety of ways which will be well known to one of skill in the art. For instance, the retainer 30 may be integrally molded such as by injection molding or by thermoplasty.

The retainer 30 preferably comprise a durably, flexible material, and more preferably comprise a generally inert, non-toxic material. In a preferred embodiment, the retainer 30 is molded of plastic, such as, for example, polycarbonate, polyvinylchloride, polypropylene, polyurethane, tetrafluoroethylene (e.g., TEFLON®), polytetrafluoroethylene (a.k.a., PTEF), acetal resin (e.g., DELRIN®), chlorotrifluoroethylene (e.g., KEL-F®), nylon or like polymers.

Second Anchoring Device

As noted above, the second anchoring device 26 of the present catheter anchoring system 10 secures a near-distal portion of the catheter body 22 to the patient's body at a point proximate to the insertion site. It also prevents axial movement of the catheter 12 so as to inhibit migration of the catheter 12 or to assist against the accidental displacement or dislodgement of the distal end of the catheter 12.

Like the first anchoring device 24, the second anchoring device 26 can take may forms. For instance, the second anchoring device 26 can be of the type illustrated in FIGS. 10–15. This exemplary embodiment is configured in accordance with the disclosure of copending application Ser. No. 29/036,141, filed Mar. 14, 1995, in the name of Steven F. Bierman, and assigned to the assignee hereof, and is hereby incorporated by reference.

In this embodiment, the second anchoring device 26 includes a flexible base pad 94. The base pad 94 is constructed in accordance with the above-description of the anchor pad 28. The adhesive layer adheres to the patient's skin in the epidural area to secure the second anchoring device 26 to the patient.

Figure 12:
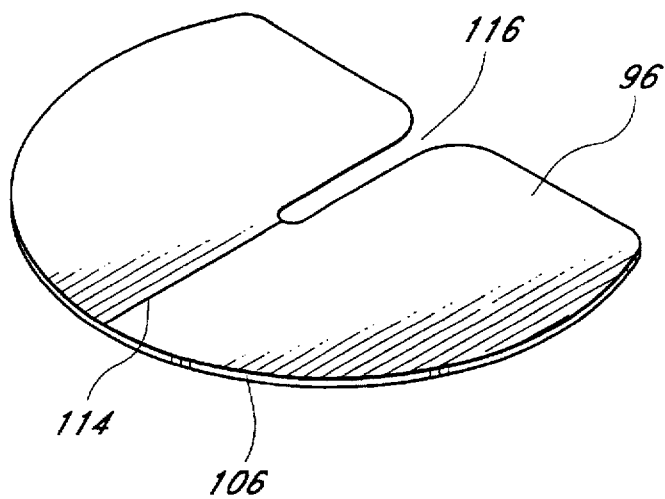
FIG. 12 is a bottom perspective view of the second anchoring device of FIG. 2.
Figure 11:
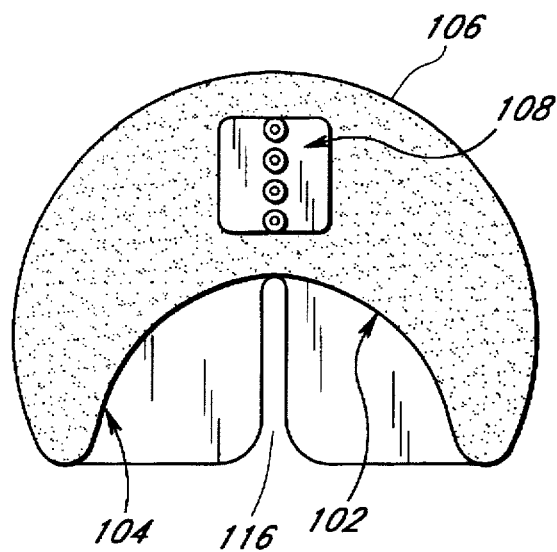
FIG. 11 is a top plan view of the second anchoring device of FIG. 2.
Figure 10:
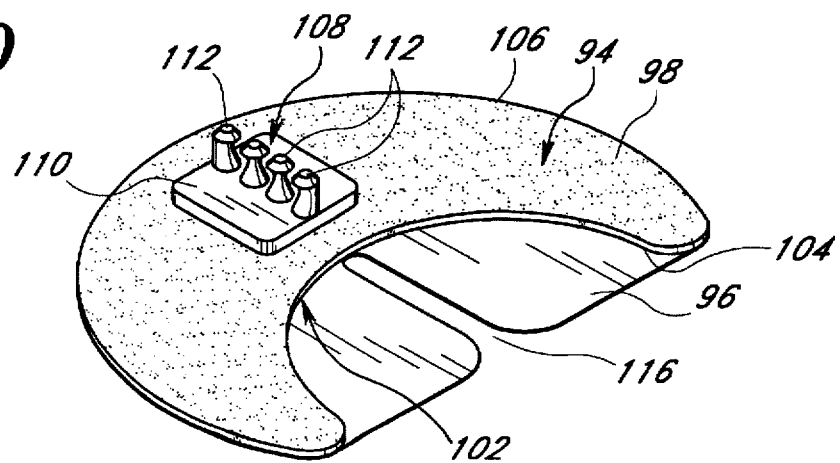
FIG. 10 is a top perspective view of the second anchoring device of FIG. 2.

As seen in FIGS. 10–12, a release layer 96 covers the adhesive bottom surface of the base pad 94 prior to use. The backing 96 preferably resists tearing and is divided into a plurality of pieces to ease attachment of the pad 94 to the patient's skin, as described below. The backing 96 desirably is split along a center line of the flexible base pad 94 in order to expose only half of the adhesive bottom surface at one time. The backing 96 also advantageously extends beyond at least one edge of the base pad 94 to ease removal of the backing 96 from the adhesive layer.

Figure 15:
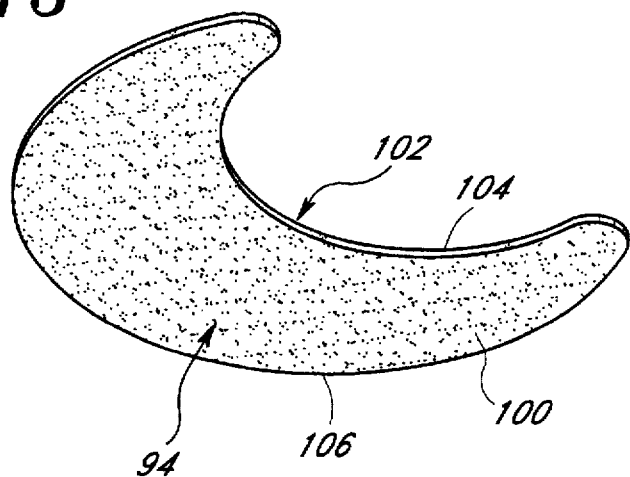
FIG. 15 is a bottom perspective view of the release layer of the second anchoring device of FIG. 2.
Figure 13:
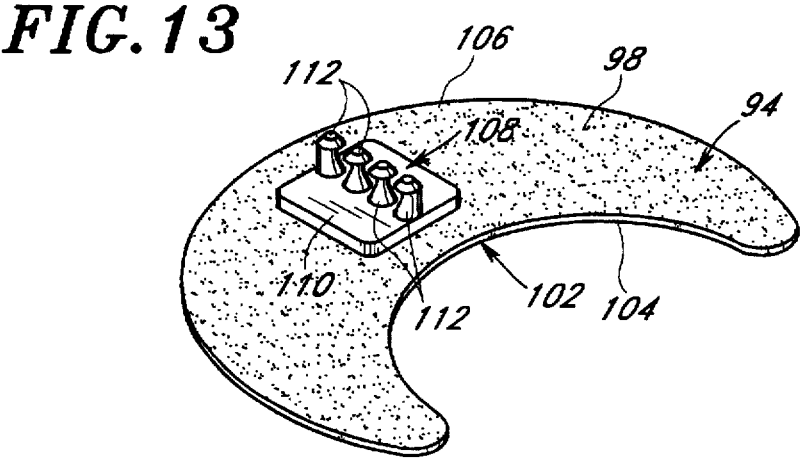
FIG. 13 is a top perspective view of the second anchoring device of FIG. 2 with a release layer.

As understood from FIGS. 13 and 15, the base pad 94 includes an upper surface 98 and a lower surface 100. In the illustrated embodiment, the lower surface 100 is defined by the adhesive bottom layer.

The base pad 94 has a recessed portion 102 formed on an inner edge 104 of the pad 94 which is desirably positioned adjacent to the point of insertion of the catheter 12 into the epidural space as illustrated in FIG. 1B. In the illustrated embodiment, the recess portion 102 has a generally concave shape. The other edge 106 of the base pad 94 can be of any shape. The recess portion 102 of the base pad 94 allows the base pad 94 to wrap around the catheter insertion site to stabilize the catheter 12. The concave shape of the recessed portion 102 also allows the health care provider to easily align the catheter 12 with the point of insertion by visually placing the concave edge 104 generally adjacent to and symmetrically to the point of insertion. Subsequently, the concave-shaped recess portion 102 allows for visual inspection of the insertion site because the insertion site is not obscured by additional bandages commonly used to stabilize the catheter 12. Visual inspection also can occur without removal of any surgical tape. The recessed shape also allows the pad 94 the more easily conform to the skin surface of the patient.

The base pad 94 supports a catheter clip 108, which is configured in accordance with the above-description. The clip 108 includes a base plate 110 with a row of retainers 112 arranged on its upper surface. Each retainer 112 includes a stem and an enlarged head which are configured as described above in connection with the catheter clip 36 of the first anchoring device 24. The base plate 110 desirably is secured to the base 94 pad by means of a light-activated adhesive (e.g., a UV activated, pressure sensitive adhesive), cyanoacrylate, or other bonding material. In the alternative, the base plate 110 can be embedded or woven into the base pad 94.

Figure 14:
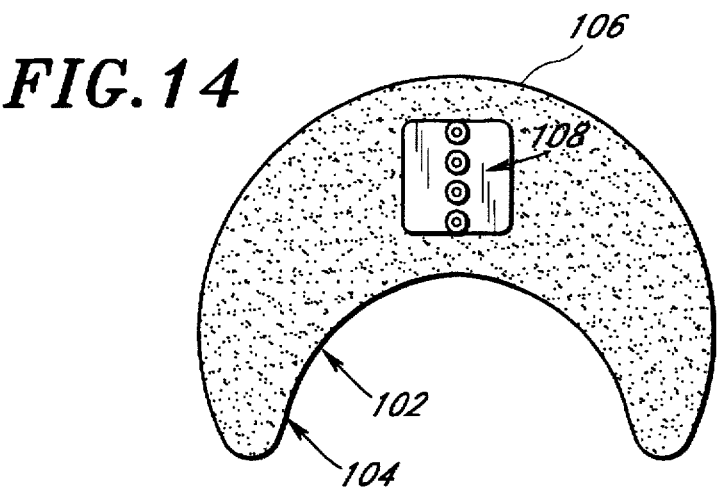
FIG. 14 is a top plan view of the second anchoring device of FIG. 2 with the release layer.

As best seen in FIGS. 11 and 14, the catheter clip 108 is attached to the upper surface 98 of the base pad 94 at a position whereby the retainers 112 of the catheter clip 108 form an axis that bifurcates the base pad 94 and is generally perpendicular to a tangent that defines the most internal point of the recessed portion 102 in the base pad 94. In the illustrated embodiment, the axis bifurcates the concave recessed portion 102.

This arrangement of the catheter clip 108 insures that axes through the channels of the catheter clip 108 lies generally transverse to the axis of the catheter 12 as it exits the insertion site. The sections of the catheter body 22, which are held by the retainers 112 of the catheter clip 110 and consequently lie generally transverse to the axis of the distal end of the catheter 12, prevent axial movement of the catheter body 22, as described below.

The base plate 110 also is positioned near the edge of the of the base pad 94. This location places the catheter clip 108 proximate to the insertion site for improved stability of the distal end of the catheter 12.

With reference to FIGS. 10–12, the release layer 96 extends beyond at least one edge of the base pad 94 to ease removal of the release layer 96 from the adhesive surface. The release layer 96 preferably extends into the area defined by the recessed portion 102 of the base pad 94 as best seen in FIG. 10. The release layer 96 is desirably divided into a plurality of pieces, preferably two pieces, to ease attachment of the pad 94 to the patient's skin as described below.

As seen in FIG. 12, the release layer 96 desirably is divided into two pieces with a split along the center line 114 of the release layer 96 in order to expose one half of the adhesive surface of the base pad 94 at a time when the release layer 96 is removed. As seen in FIGS. 10–12, the split along the center line 114 is expanded to form a wider longitudinal opening 116 in the area of the release layer 96 that occupies the area defined by the concave recessed portion 102 of the base pad 94. The longitudinal opening 116 is aligned with the axis defined by the retainers 112 of the catheter clip 108. In this manner, the longitudinal opening 116 facilitates alignment of the retainers 112 of the catheter clip 108 with the axis of the catheter 12 exiting the insertion site.

Figure 17:
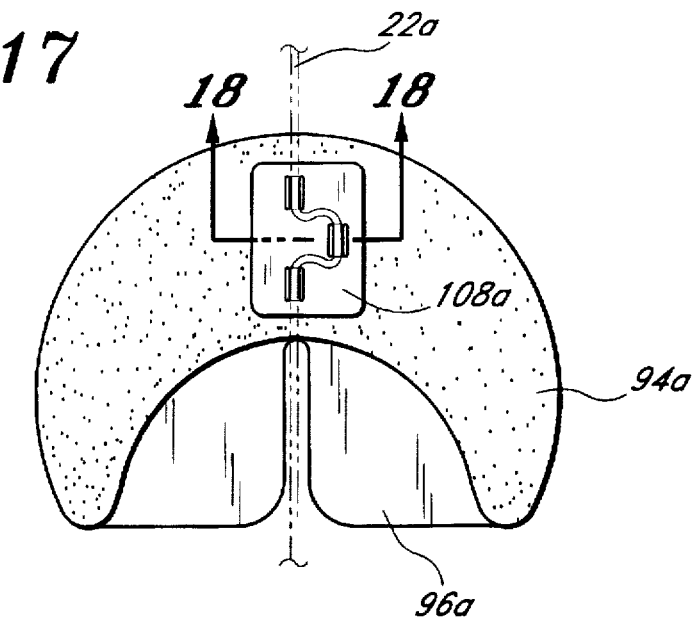
FIG. 17 is a top plan view of the second anchoring device of FIG. 16, illustrating a retainer second in phantom lines.
Figure 18:
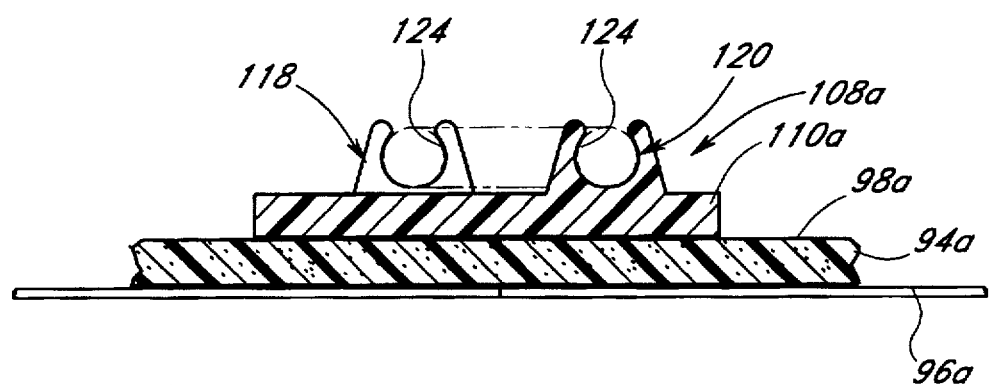
FIG. 18 is a cross-section view of the second anchoring device of FIG. 16 taken along the line 18—18.
Figure 16:
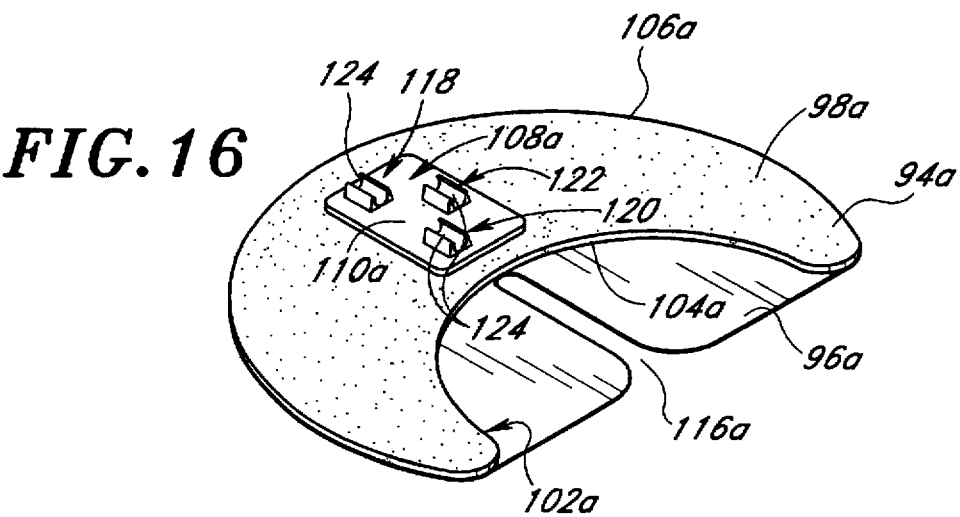
FIG. 16 is a top perspective view of a second anchoring device configured in accordance with another embodiment of the present invention, with a release layer.

FIGS. 16–18 illustrate another embodiment of the second anchoring device. In this embodiment, a base pad and associated release layer are configured and constructed in accordance of the above-description of the corresponding components. Accordingly, the above-description of the base pad and release layer will apply equal to base pad and release layer of this embodiment, unless specified to the contrary. For ease of understanding, like references with an "a" suffix will be used to designate like part of the two embodiment.

The catheter clip 108 includes a base plate 110a with a plurality of retainers having a shape similar to that of the tube clip 43 described above. As illustrated in FIG. 16, the retainers are aligned on the base plate 110a such that a proximal retainer 118 and a distal retainer 120 define an axis which bisects the recess portion 102a of the base pad 94a. A middle retainer 122 is offset from the axis. This arrangement of the retainers 118, 120, 122 on the base plate 110a causes at least a portion of the catheter body 22a to lie generally transverse to the axis (which typically is aligned with the axis of the catheter body 22a exiting the insertion site) to prevent axial movement of the catheter body 22a.

Each retainer 118, 120, 122 defines a central channel 124 having a generally circular cross-section configuration truncated at the top to form an upper orifice into which the catheter body 22a (shown in phantom lines) is inserted by positioning the catheter body 22a over the orifice and pressing downwardly on the catheter body 22a or gently pulling the catheter tube across the orifice. The diameter of the central channel 124 of the retainer is slightly smaller than the outer diameter of the catheter body 22a to hold the catheter body 22a inserted into the retainer but not to significantly occlude an inner lumen of the catheter body 22a. When the catheter body 22a has been inserted into the central channel 124, the retainer surrounds a substantial portion of the circumference of the catheter body 22a.

The upper edges of the central channel 124 are preferably tapered to form a smooth rounded transition between the central channel and the upper edge. Tapered rounded ends may also be provided at the proximal and distal ends of the retainers 118, 120, 122. Tapered ends help to guide the catheter body 22a into the central channel 124 of the retainer when the catheter body is pressed or gently pulled into the central channel 124.

FIGS. 19–22 illustrate an additional embodiment of the second anchoring device which is substantially identical in form and construction to the second anchoring device described above in connection with FIGS. 16–18. The embodiment of FIGS. 19–22 includes additional retainer sets which are arranged differently on the base pad. Accordingly, like reference numerals with a "b" suffix have been used to identify like components of the two embodiments for ease of understanding.

The catheter clip 108b includes a plurality of retainers of different diameter sizes attached to the base plate 110b for securing different sizes of catheter tubing. For instance, in the illustrated embodiment, the catheter clip 108b has five sets of retainers. Each set has three retainers: a proximal retainer 118b, a middle retainer 122b and a distal retainer 120b. All the retainers within a set have a central channel 124b with the same diameter size. Between the retainer sets, however, the diameter sizes of the central channels 124b differ to secure five sizes of catheter bodies 22b.

Figure 19:
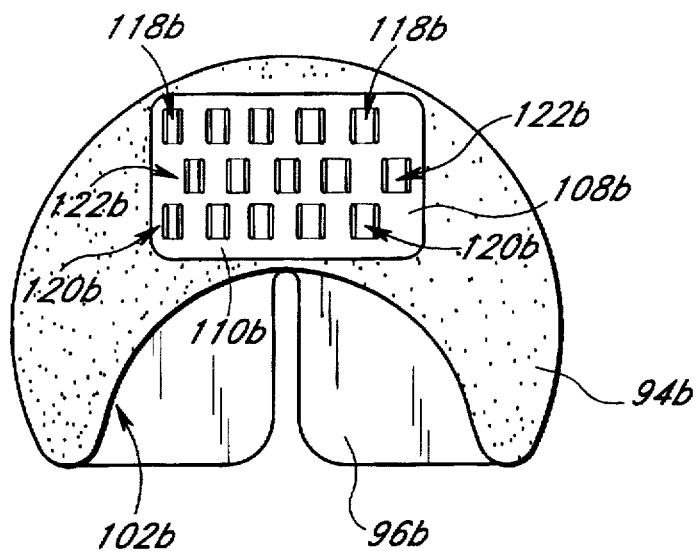
FIG. 19 is a top plan view of a second anchoring device configured in accordance with an additional embodiment of the present invention with a release layer, the bottom side looking identical to the design shown in FIG. 12.
Figure 20:
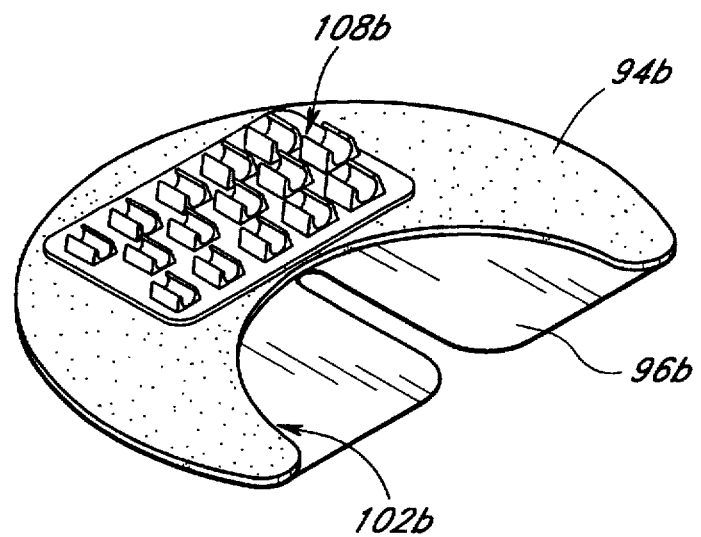
FIG. 20 is a top prospective view of the second anchoring device shown in FIG. 19.
Figure 21:
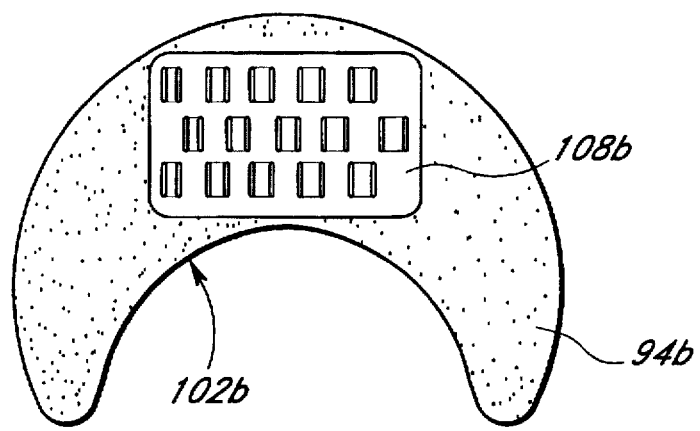
FIG. 21 is a top plan view of the second anchoring device of FIG. 19 without the release layer, the bottom side looking identical the design shown in FIG. 15.
Figure 22:
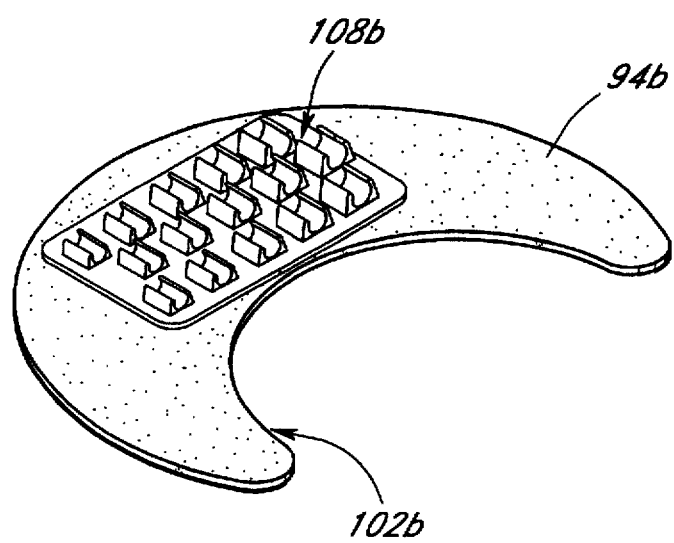
FIG. 22 is a top prospective view of the second anchoring device shown in FIG. 21.

In the illustrated embodiment of FIG. 19, a first set of retainers on the left side of the base plate 110b includes a proximal retainer 118b, a middle retainer 122b and a distal retainer 124b, all of the same smallest size present on this catheter clip (e.g., 18 gauge). The proximal and distal retainers 118b, 120b define an axis from which the middle retainer 122b is slightly offset.

Each set of retainers comprises a single size of proximal, middle and distal retainers similarly arranged, with each set being a size larger than the previous set moving from left to right. Preferably, the retainers sets are sized to accept 18, 19, 20, 21 and 22 gauge catheter tubing.

In use, the health care provider presses the catheter tubing 22b into the retainer or snakes the catheter tubing 22b through the retainers, selecting the appropriate size retainer set for the catheter tubing being used. It will be understood that the catheter clip 108b of this embodiment could have fewer or more sets of retainers and the retainers could be sized to accept other sizes of catheter tubing than those illustrated here.

It is appreciated that any of the catheter clip embodiments described in connection with the second anchoring device also can be used with the first anchoring device. That is, the embodiment illustrated in FIGS. 15–18 or the embodiment illustrated in FIGS. 19–22 can be included on the anchor pad 28 of the first anchoring device 24.

It also is understood that the present anchoring system 10, which includes the first and second anchoring devices 24, 26, can be packaged in a kit with a catheter 12, needle, cannula, and like instruments. A health care provider can perform the catheterization procedure using the components of the kit as described below.

Method of Use

The following method of use will be with reference principally to FIG. 1 and FIG. 2, and will be in the context of epidural catheterization. This discussion of the method of use is meant to augment the description of the invention above and both should be read together.

The health care provider begins epidural catheterization by inserting the distal end of the epidural catheter body 22 into the epidural space using well known procedures. For example, prior to insertion of the epidural catheter 12, a needle or other stylus is inserted into the epidural space. Then, the distal end of the epidural catheter 12 is inserted through the cannula portion of the needle into the epidural space and the needle is withdrawn leaving the catheter inserted. The epidural catheter 12 is primed with sterile fluid in the usual manner to ensure flow of fluid through the system.

After priming the catheter 12, the health care provider inserts the extension set 38 between the fluid supply line 20 and the catheter 12. The female luer lock on the proximal end of the extension set 38 is attached to the distal end of the fluid supply tube 20. A filter can be attached between the fluid supply tube 20 and the extension set 38 if desired or deemed necessary. The health care provider then primes the extension set 38 (and filter is used) with sterile normal saline solution.

The catheter 12 is attached to the catheter adaptor 32 of the extension set 38. The Tuoghy-Borst connector 14 is tightly connected to the lure-lock fitting 46 on the distal end of the catheter adaptor 32.

The second anchoring device 26 is used to stabilize the catheter 12 at the insertion site. The health care provider prepares the skin around the insertion site by applying alcohol and letting it dry.

While holding the base pad 94 of second anchoring device 26 with the recessed portion 102 adjacent to the insertion site, the health care provider threads the catheter body 22 around the retainers 112 of the clip 108 to form a generally serpentine shape. This may be done by first forming a U-shaped loop in the catheter body 22 and then gently pressing each leg of the loop into the correspond channel of the clip 108. Once inserted, the health care provider gently tightens the catheter 12 around the retainers 112 by pulling on the proximal side of the catheter 12 to remove the slack.

If the second anchoring device 26 is of the type illustrated in FIGS. 16–18 or 19–22, the catheter body 22 is snaked through the central channels 124 of the retainers 118, 120, 122, pressing gently using finger pressure or drawing the catheter body into the central channels 124 of the retainers. It will be understood that if the catheter anchoring device 26 illustrated in FIGS. 19–22 is used, the health care provider will position the catheter body 22 in the set of retainers appropriate for the size of catheter body 22 in use.

The health care provider places the concave recessed portion 102 of the base pad 94 of the catheter anchoring device 26 within a few centimeters of the point of catheter insertion by positioning the catheter within the longitudinal opening 116 of the release layer 96 before removing one of the halves of the release layer 96. In the alternative, if one half of the release layer 96 is already removed, then the health care provider can align the remaining side of the longitudinal opening 116 in the release layer 96 with the catheter 12.

The health care provider removes the release layer 96 of the catheter anchoring device 26 by grasping one of the exposed ends of the release layer 96 and pealing one half of the release layer 96 away from the base pad 94 thus exposing the adhesive lower surface of the base pad 94. The exposed adhesive surface is gently pressed onto the patient's skin by pressing on the upper surface 98 of the base pad 94 to attach the device to the skin proximal to the point of insertion of the epidural catheter 12. The second half of the release layer 94 is similarly removed and the exposed adhesive lower surface of the base pad 94 is gently pressed onto the patient's skin as above to complete application of the second anchoring device 26 proximate to the insertion site as shown in FIG. 1B. Alternatively, health care provider may remove both halves of the release layer 96 and position the device 26 proximate to the epidural catheterization point by visually aligning the retainers 112 with the catheter 12 and placing the concave recessed portion 102 of the base pad 94 near the catheter entry point into the skin. Any indicia on the release layer 96 or the base pad 94 (e.g. arrows, dots, words, graphics) may be used by the health care provider to facilitate positioning of the device proximate to the epidural catheterization point or to aid in removal of the release layer 96 from the base pad 94.

The catheter body 22 is looped around the patient's torso to the front of the torso near where the first element 24 of the catheter anchoring system 10 shown in FIG. 1A will be placed on the patient's skin (e.g., on the abdomen or chest). The health care provider prepares the anticipated dressing site per hospital protocol and allows the site to dry thoroughly.

The catheter body 22 is then placed into the clip 36 of the first anchoring device 24 in the same manner described above in connection with the clip 108 of the second anchoring device 26. The health care provider inserts the catheter adaptor 32, which is already attached to the catheter 22, into the cradle or retainer 30 of the first anchoring device 24. In doing so, the health care provider positions the catheter adaptor 32 over the central channel 52 and snaps the body 44 into the channel 52. The collar or collars 50 insert into the slots 56 thus preventing the body 44 of the adaptor 32 from moving in a longitudinal direction through the central channel 52 of the retainer 30.

The health care provider then secures the tube segment 40 of the extension set 38 to the anchor pad 28. The tube segment 40 is placed over the tube clip 34 and then gently pressed into the channel 64 of the clip 34. The health care provider leaves sufficient slack in the tube segment 40 to avoid kinking and to form a conventional safety loop.

It will be understood by those skilled in the art that the sequence of making connections between the catheter Tuoghy-Borst connector 14, the adaptor 32 and the fluid tube 20 can be varied according to the usual procedures of the health care provider. Similarly, the order of placement of the catheter body 22 in the catheter clip 36 and the tube segment 40 of the extension set 38 in the tube clip 34 can be varied.

After the catheter adaptor 32, catheter body 22 and tube 40 have been connected to the first anchoring device 24, the release layer (not shown) of the anchor pad 28 is removed essentially as described above. The health care provider positions the first anchoring device 24 over the target area on the patient's chest, abdomen or other accessible area and gently presses the upper surface of the base pad 28 to secure the adhesive lower surface to the patient's skin as shown in FIG. 1A. It will be understood by those skilled in the art that the position of the anchor pad 28 is not critical and it can be positioned to allow the health care provider easy access to the fluid supply tube 20 for replacement of the tube 20 as needed. However, placement of the first element 24 of the catheter anchoring system 10 on the front of the patient's body generally provides greater comfort to the patient by allowing the patient to lie on his or her back during catheterization.

The anchoring device of this invention is useful for securing a catheter in close proximity of the insertion site (e.g., within a few centimeters) to prevent the catheter from dislodging or migrating from the point of effectiveness following insertion into the patient's body. The present invention includes a useful method for securing a catheter system to a patient's body where the catheter and interconnecting device for attachment of the catheter to a fluid supply are attached to one portion of the patient's body and the catheter is inserted into another portion of the patient's body some distance away. This method is particularly important for securing an epidural catheter in which the catheter body and a fluid supply tube interconnection are anchored to the front of a patient's torso and the epidural catheter is secured on the patient's back near the point of catheterization. This method is useful because it prevents the patient from lying on the fluid supply interconnection, facilitates attachment and reattachment of the fluid supply to the catheter by medical personnel, and secures the catheter proximal to the point of insertion into the patient's body thus preventing the catheter from dislodging or migrating away from the insertion site.

In sum, the present anchoring system reduces catheter dislodgement, disconnection and migration, especially with long-term epidural catheters. It also standardizes securement protocol and enhances safety and stability. The elimination of surgical tape also allow the health care provider to visually inspect all connections between the catheter and the fluid delivery system, as well as between these components and the anchoring system.

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. A catheter anchoring device for securing an indwelling catheter proximate to a point of insertion of the catheter into a body lumen of a patient comprising:

a flexible anchor pad having an upper surface and a lower surface, said lower surface being defined at least in part by an adhesive layer which releasably adheres to the patient's skin, said upper and lower surfaces together defining an edge that includes a recessed portion positioned on a side of the pad; and a clip comprising a plurality of channels to receive a section of a flexible tubular body of the catheter, said channels being supported by said anchor pad and being only positioned behind said recessed portion, each channel including an axis through the channel, and said channels being arranged on the anchor pad in a manner offsetting the axes of the channels from one another such that a portion of the received catheter body section lies generally transverse to an axis bifurcating the recessed portion.

2. The catheter anchoring device of claim 1, wherein at least one of said channels of said clip lies generally transverse to said axis.

3. The catheter anchoring device of claim 2, wherein said clip further comprises a base plate and at least three retainers that define said channels, each of said retainers comprising a stem extending upwardly from said base plate and an expanded head supported by said stem, said retainers lying generally along said axis bifurcating said recessed portion of said anchor pad.

4. The catheter anchoring device of claim 3, wherein each channel is defined between the stems and the expanded heads of adjacent retainers.

5. The catheter anchoring device of claim 4, wherein said stems are spaced from one another by a distance at least generally equal to the diameter of the catheter body, and said expanded heads are spaced from one another by a distance less than the diameter of the catheter body.

6. The catheter anchoring device of claim 1, wherein at least one of said channels lies generally parallel to said axis.

7. The catheter anchoring device of claim 6, wherein said clip further comprises a base and at least three retainers, each of said retainers defines one of said channels of said clip, the channel of each retainer has a C-shaped cross-sectional shape of a diameter at least generally equal to the diameter of the catheter body, with an opening that has a width smaller that the diameter of the catheter body.

8. The catheter anchoring device of claim 6, wherein said retainers are positioned such that at least two of said retainers lie generally along said axis bifurcating said recessed portion of said anchor pad and at least one retainer is offset from said axis.

9. The catheter anchoring device of claim 6, wherein said clip further comprises a plurality of retainer groups, each retainer group comprising at least three retainers with the channels of the retainers within a group being of the same diameter size.

10. The catheter anchoring device of claim 9, wherein the diameter size of the channels within one group differs from the diameter size of the channels within another group.

11. The catheter anchoring device of claim 9, wherein the retainers of each retainer group are positioned with at least two of said retainers lying along a common axis and at least one retainer lying to the side of the common axis.

12. The catheter anchoring device of claim 1 additionally comprising a release layer covering said adhesive layer, said release layer being divided along a line.

13. The catheter anchoring device of claim 1, wherein said recessed portion has a generally concave shape.

14. The catheter anchoring device of claim 1, wherein said channels are sized to receive a section of an epidural catheter body.

15. The catheter anchoring device of claim 1, wherein said clip is attached to said anchor pad by a light activated adhesive.

16. The catheter anchoring device of claim 15, wherein said light sensitive adhesive is a UV activated, pressure-sensitive adhesive.

17. A catheter anchoring device for securing an indwelling catheter proximate to a point of insertion of the catheter into a body lumen of a patient, said anchoring device comprising a flexible anchor pad having an adhesive layer which releasably adheres to the patient's skin, said anchor pad including a recess positioned on a side of the pad, and means for inhibiting movement of a section of the catheter body relative to said anchor pad, said means being attached to said anchor pad and positioned to generally align with a center line of said recess.

18. The catheter anchoring device of claim 17, wherein said recess generally has a concave shape.

19. The catheter anchoring device of claim 17, wherein said means for inhibiting movement of a section of the catheter body defines a plurality of channels which receive the catheter body section, at least one of said channels being positioned generally transverse to the center line of said recess.

20. The catheter anchoring device of claim 17, wherein said means for inhibiting movement of a section of the catheter body defines a plurality of channels which receive the catheter body section, at least one of said channels being positioned generally parallel to the center line of said recess.

21. The catheter anchoring device of claim 17, wherein said means for inhibiting movement of the catheter body section receives the catheter body section in a manner giving the catheter body section a generally serpentine shape.

22. A catheterization kit comprising:

a first catheter anchoring device including a flexible anchor pad having an adhesive surface which releasably adheres to a patient's skin, said anchor pad supporting a cradle for a catheter adaptor, said catheter adaptor configured to interconnect a tube with a catheter; and a second catheter anchoring device including a flexible anchor pad having an adhesive surface which releasably adheres to a patient's skin, and a clip comprising a plurality of channels to receive a section of a flexible tubular body of the catheter, said channels being arranged on said anchor pad to give the received catheter body section a serpentine shape, said anchor pad supporting said clip.

23. The catheterization kit of claim 22 additionally comprising a catheter.

24. The catheterization kit of claim 22, wherein said anchor pad of said second anchoring device includes a recess positioned about an axis bifurcating said recess, and said channels are arranged on said anchor pad relative to said recess such that a portion of said received catheter body section lies generally transverse to said axis.

25. The catheterization kit of claim 24, wherein said recessed portion of said second anchor pad is generally concave in shape.

26. The catheterization kit of claim 24, wherein at least one of said channels of said clip lies generally transverse to said axis.

27. The catheterization kit of claim 24, wherein at least one of said channels lies generally parallel to said axis.

28. The catheterization kit of claim 27, wherein said clip further comprises a base and at least three retainers, each of said retainers defines one of said channels of said clip, the channel of each retainer has a C-shaped cross-sectional shape of a diameter at least generally equal to the diameter of the catheter body, with an opening that has a width smaller than the diameter of the catheter body.

29. The catheterization kit of claim 27, wherein said retainers are positioned such that at least two of said retainers lie generally along said axis bifurcating said recess of said anchor pad and at least one retainer is offset from said axis.

30. The catheterization kit of claim 22, wherein said first anchoring device includes a clip comprising a plurality of channels to receive another section of the flexible tubular body of the catheter, said channels being arranged on said base to give the received catheter body section a serpentine shape, said anchor pad supporting said clip.

31. The catheterization kit of claim 30, wherein the clips of said first and second anchoring devices each comprise a base plate and at least three retainers that define said channels, each of said retainers comprising a stem extending upwardly from said base plate and an expanded head supported by said stem, said retainers generally being aline with one another.

32. The catheterization kit of claim 31, wherein each channel is defined between the stems and the expanded heads of adjacent retainers.

33. The catheterization kit of claim 32, wherein said stems are spaced from one another by a distance at least generally equal to the diameter of the catheter body, and said expanded heads are spaced from one another by a distance less than the diameter of the catheter body.

34. The catheterization kit of claim 30, wherein said clip of said first anchoring device is attached the corresponding anchor pad by a light activated adhesive, and said clip of said second anchoring device is attached to the corresponding anchor pad by a light activated adhesive.

35. The catheterization kit of claim 34, wherein said light activated adhesive is a UV activated, pressure sensitive adhesive.

36. The catheterization kit of claim 22, wherein said catheter adaptor of said first anchoring device comprises a generally tubular body defined between a distal end configured to engage a proximal end of the catheter and a proximal end configured to couple with a distal end of the tube, and at least one radially extending member with projects from said tubular body.

37. The catheterization kit of claim 36, wherein said cradle of said first anchoring device comprises a longitudinal channel configured to receive said tubular body of said adaptor in a snap-fit manner, and at least one lateral slot sized to receive and to capture said radially extending member of said adaptor with said adaptor positioned within said longitudinal channel.

38. A method of securing an indwelling catheter within a body lumen of a patient proximate to a point of insertion of the catheter into the body lumen comprising the steps of:

providing a flexible anchor pad including an adhesive layer which releasably attaches to the patient's skin, and a clip supported by said anchor pad, said clip configured to receive a section of the catheter body such that at least a portion of the catheter body section lies generally transverse to a center line of a recessed portion of said anchor pad;

positioning said anchor pad proximate to the point of insertion of the catheter;

threading an elongated section of the catheter body through said clip in a direction away from the insertion site;

positioning at least a portion of the catheter body section within the clip such that said portion within the clip lies generally transverse to the center line of the recessed portion of the anchor pad; and applying said flexible anchor pad to the patient's skin proximate to the point of insertion of said catheter.

39. The method of claim 38, wherein threading involves positioning said flexible tubular section of said catheter body through channels of said clip.

40. The method of claim 39, wherein positioning the catheter body into said channels involves inserting the catheter body section between expanded heads and stems of retainers of said clip which define said channels.

41. The method of claim 39, wherein positioning the catheter body into said channels involves inserting the catheter body through an opening of the channel defined by a retainer of the clip, the channel having a C-shaped cross-sectional shape.

42. The method of claim 38, wherein positioning involves locating at least one side of an elongated opening of a release layer on said anchor pad generally parallel to an axis of said indwelling catheter, and applying involves removing said release layer before pressing said adhesive layer onto the patient's skin.

43. A method of securing an indwelling epidural catheter to the body of a patient comprising the steps of:

providing a first anchor pad having an adhesive surface which releasably attaches to a patient's skin and supports retainer for holding a catheter adaptor body;

providing a second anchor pad having an adhesive surface which releasably attaches to a patient's skin and supports clip for receiving a flexible tubular portion of said catheter, said clip having a plurality of channels which receive a portion of the flexible catheter body, said channels being arranged on a base of said clip to give the received flexible catheter body a serpentine shape with the catheter body inserted in adjacent channels;

positioning said second anchor pad proximate to the point of insertion of said epidural catheter;

threading a portion of said catheter body through the channels of said clip of said second anchor pad such that said threaded portion generally has a serpentine shape;

applying said second anchor pad to the patient's skin proximate to the point of insertion of said epidural catheter by pressing said adhesive surface onto the patient's skin;

extending said catheter to a position on the patient's body away from said point of insertion of said epidural catheter;

attaching a catheter adaptor to said epidural catheter;

attaching a fluid supply tube to said catheter adaptor;

placing said catheter adaptor into said retainer on said first anchor pad; and applying said first anchor pad to the patient's skin at a position distanced from the point of insertion of the epidural catheter by pressing the adhesive surface to the patient's skin.

44. The method of claim 43, wherein threading a portion of said catheter body through said channel of said clip involves positioning a portion of the flexible tubular body of said catheter in a position generally transverse to an axis which bifurcates a recessed portion of said anchor pad.

45. The method of claim 44, wherein positioning said second anchor pad involves placing said recessed portion of said anchor pad proximate to said point of insertion and aligning said axis with said point of insertion.

46. The method of claim 43 additionally comprising the steps of:

threading a portion of said catheter body through a clip on said first anchor pad;

attaching said fluid tube to a tube clip on said first anchor pad.

* * * * *